(12) United States Patent
Eberle et al.

(10) Patent No.: US 6,899,682 B2
(45) Date of Patent: May 31, 2005

(54) INTRAVASCULAR ULTRASOUND TRANSDUCER ASSEMBLY HAVING A FLEXIBLE SUBSTRATE AND METHOD FOR MANUFACTURING SUCH ASSEMBLY

(75) Inventors: Michael J. Eberle, Fair Oaks, CA (US); P. Michael Finsterwald, Phoenix, AZ (US)

(73) Assignee: Volcano Therapeutics, Inc., Rancho Cordova, CA (US)

( * ) Notice: Subject to any disclaimer, the term of this patent is extended or adjusted under 35 U.S.C. 154(b) by 0 days.

(21) Appl. No.: 10/661,269

(22) Filed: Sep. 12, 2003

(65) Prior Publication Data

US 2004/0054289 A1 Mar. 18, 2004

Related U.S. Application Data

(60) Continuation of application No. 09/550,864, filed on Apr. 17, 2000, now Pat. No. 6,618,916, which is a continuation of application No. 08/974,677, filed on Nov. 19, 1997, now Pat. No. 6,049,958, which is a division of application No. 08/780,437, filed on Jan. 8, 1997, now Pat. No. 5,857,974.

(51) Int. Cl.[7] ............................................. A61B 8/14
(52) U.S. Cl. .................................... 600/459; 600/467
(58) Field of Search .............................. 600/437–472; 29/25.35, 594; 310/333–336

(56) References Cited

U.S. PATENT DOCUMENTS

| | | | |
|---|---|---|---|
| 3,827,115 A | 8/1974 | Bom | |
| 3,938,502 A | 2/1976 | Bom | |
| 4,191,193 A | 3/1980 | Seo | |
| 4,211,949 A | 7/1980 | Brisken et al. | |
| 4,456,013 A | 6/1984 | De Rossi et al. | |
| 4,576,177 A | 3/1986 | Webster, Jr. | |
| 4,582,067 A | 4/1986 | Silverstein et al. | |
| 4,645,961 A | 2/1987 | Malsky | |
| 4,665,331 A | 5/1987 | Sudo et al. | |
| 4,665,925 A | 5/1987 | Millar | |
| 4,704,774 A | 11/1987 | Fujii et al. | |
| 4,728,834 A | 3/1988 | Kumar et al. | |
| 4,734,963 A | 4/1988 | Ishiyama | |
| 4,794,931 A | 1/1989 | Yock | |
| 4,821,731 A | 4/1989 | Martinelli et al. | |

(Continued)

FOREIGN PATENT DOCUMENTS

| | | |
|---|---|---|
| EP | 0145429 | 6/1985 |
| EP | 0671221 | 9/1995 |
| GB | 2208138 B | 3/1989 |
| GB | 2208138 A | 3/1989 |
| GB | 2287375 A | 9/1995 |
| JP | 54149615 | 11/1979 |
| NL | 1 402 192 | 2/1972 |
| WO | WO 88/09150 | 12/1988 |

(Continued)

OTHER PUBLICATIONS

Lockwood et al., "A 45 to 55 MHz Needle–Based Ultrasound System for Invasive Imaging," *Ultrasonic Imaging*, 15 (1), 1–13 (Jan. 1993).

(Continued)

*Primary Examiner*—Ali Imam
(74) *Attorney, Agent, or Firm*—Leydig, Voit & Mayer, LTD

(57) ABSTRACT

The present invention comprises methods for fabricating an ultrasound transducer assembly having a flexible circuit. Preferably, the method comprises attaching an ultrasound transducer array and integrated circuitry to the flexible circuit during fabrication of the ultrasound transducer assembly while the flexible circuit is in a substantially flat shape. The contacts of the transducer elements are positioned on substantially the same plane such that electrical contact with signal and ground lines on the flexible circuit is established without the need for conductive bridges to physically remote electrodes.

10 Claims, 13 Drawing Sheets

U.S. PATENT DOCUMENTS

| | | |
|---|---|---|
| 4,841,977 A | 6/1989 | Griffith et al. |
| 4,917,097 A | 4/1990 | Proudian et al. |
| 4,951,677 A | 8/1990 | Crowley et al. |
| 4,975,607 A | 12/1990 | Hara et al. |
| 5,042,493 A | 8/1991 | Saito et al. |
| 5,044,053 A | 9/1991 | Kopel et al. |
| 5,046,503 A | 9/1991 | Schneiderman |
| 5,081,993 A | 1/1992 | Kitney et al. |
| 5,109,860 A | 5/1992 | Gelly et al. |
| 5,117,831 A | 6/1992 | Jang et al. |
| 5,174,296 A | 12/1992 | Watanabe et al. |
| 5,176,141 A | 1/1993 | Bom et al. |
| 5,183,048 A | 2/1993 | Eberle |
| 5,186,177 A | 2/1993 | O'Donnell et al. |
| 5,199,437 A | 4/1993 | Langberg |
| 5,240,003 A | 8/1993 | Lancee et al. |
| 5,243,988 A | 9/1993 | Sieben et al. |
| 5,257,629 A | 11/1993 | Kitney et al. |
| 5,273,045 A | 12/1993 | Chihara et al. |
| 5,320,104 A | 6/1994 | Fearnside et al. |
| 5,351,691 A | 10/1994 | Brommersma |
| 5,359,760 A | 11/1994 | Busse et al. |
| 5,368,037 A | 11/1994 | Eberle et al. |
| 5,402,791 A | 4/1995 | Saitoh et al. |
| 5,423,220 A | 6/1995 | Finsterwald et al. |
| 5,453,575 A | 9/1995 | O'Donnell et al. |
| 5,467,779 A | 11/1995 | Smith et al. |
| 5,479,930 A | 1/1996 | Gruner et al. |
| 5,493,541 A | 2/1996 | Snyder |
| 6,049,958 A * | 4/2000 | Eberle et al. .............. 29/25.35 |
| 6,618,916 B1 * | 9/2003 | Eberle et al. .............. 29/25.35 |

FOREIGN PATENT DOCUMENTS

| | | |
|---|---|---|
| WO | WO 89/04142 | 5/1989 |
| WO | WO 93/02809 | 2/1993 |
| WO | WO 93/15419 | 8/1993 |

OTHER PUBLICATIONS

Martin et al., "An Ultrasonic Catheter for Intravascular Measurement of Blood flow; Technical Details," *IEEE, SU* 27 (6), 277–286 (Nov. 1980).

Black et al., "CMOS Chips for Invasive Ultrasound Imaging," *IEEE Journal of Solid–State Circuits* 29 (11), 1381–1387 (Nov. 1994).

Bom et al., "Early and Recent Intraluminal Ultrasound Devices," *International Journal of Cardiac Imaging*, 4, 79–88 (1989).

O'Donnell et al., "Experimental Studies on an Efficient Catheter Array Imaging System," *Ultrasonic Imaging*, 17 (2), 83–94 (1995).

* cited by examiner

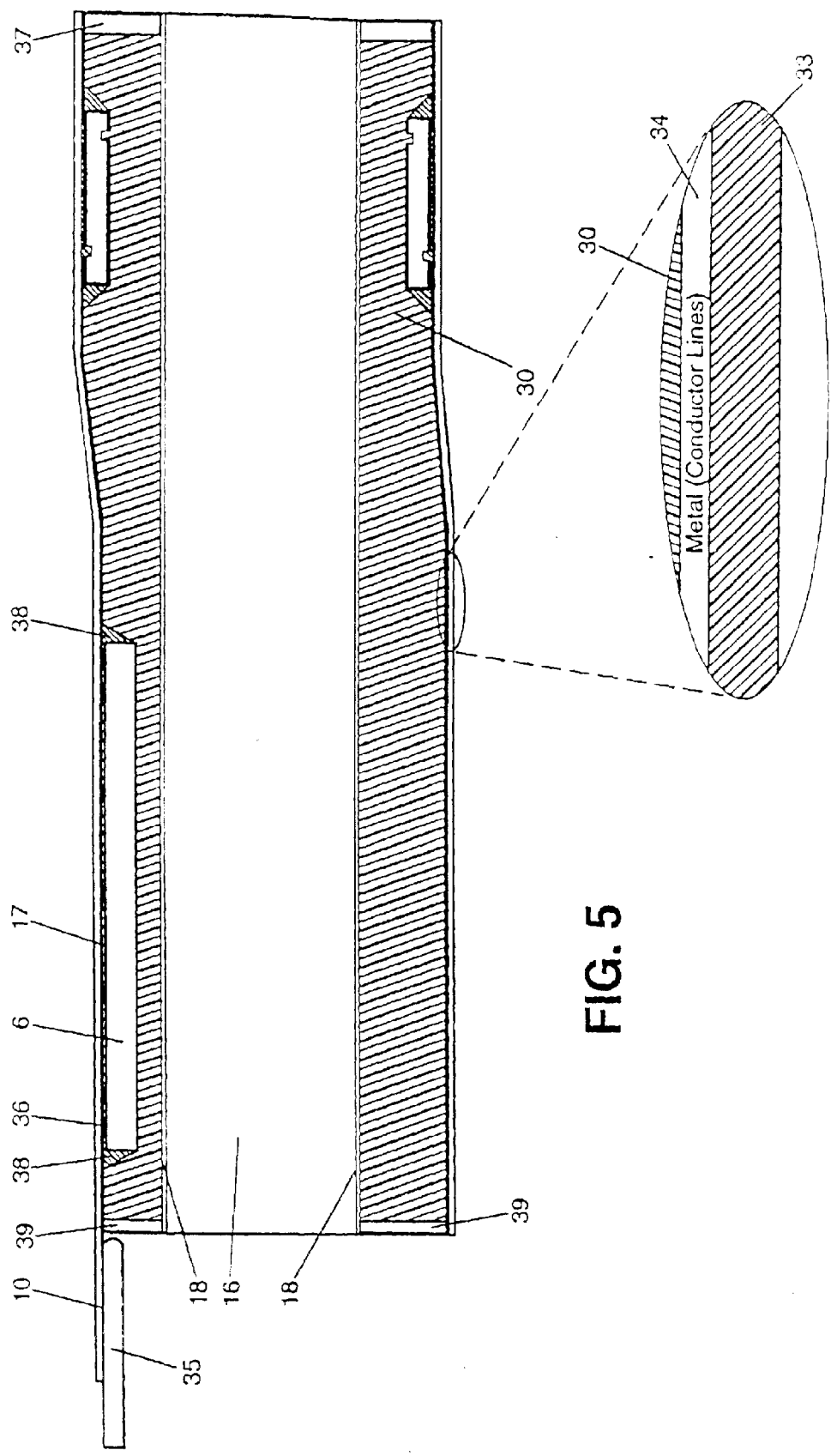

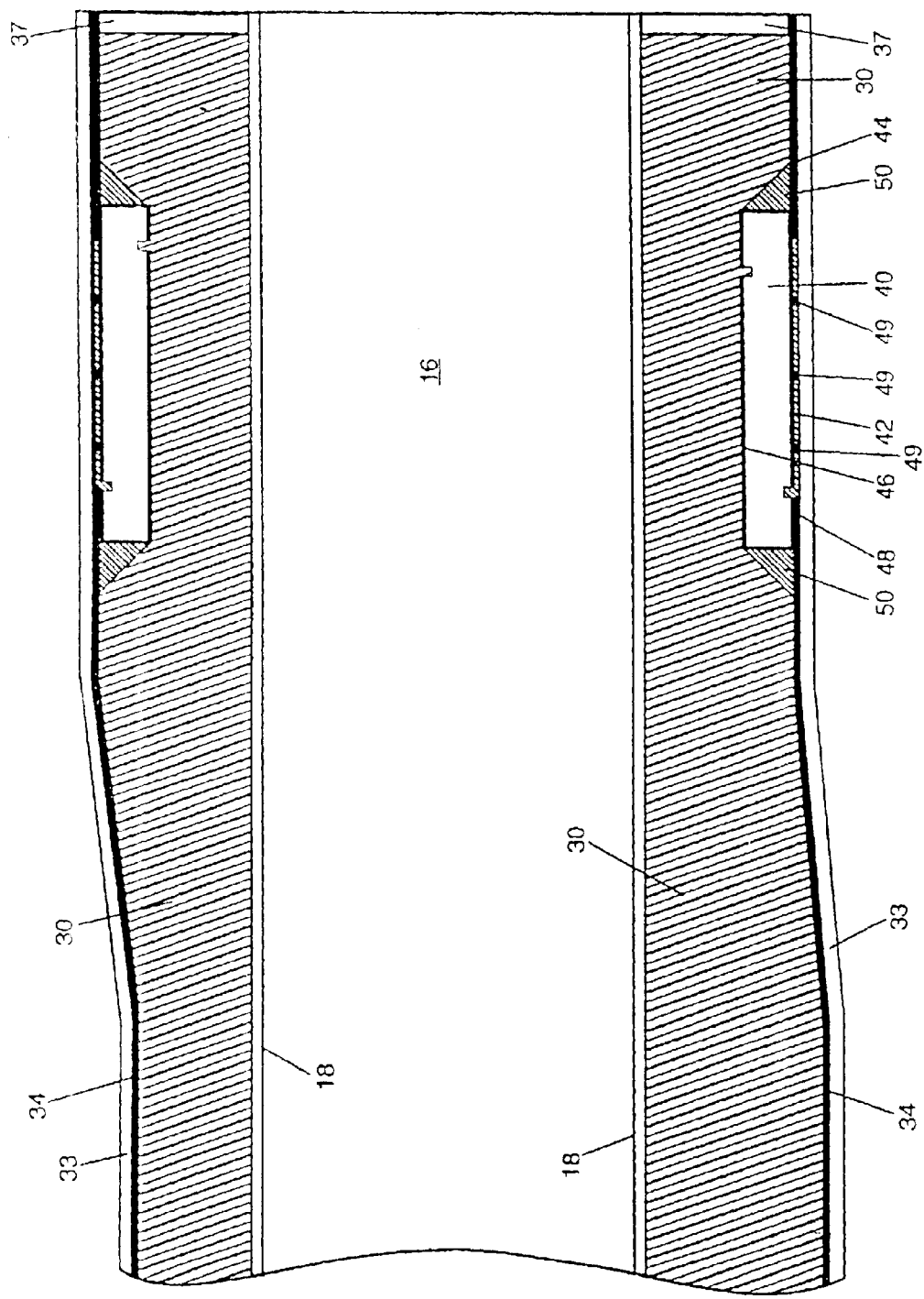

INTRAVASCULAR ULTRASOUND TRANSDUCER ASSEMBLY HAVING A FLEXIBLE SUBSTRATE AND METHOD FOR MANUFACTURING SUCH ASSEMBLY

This application is a continuation of Ser. No. 09/550,864, filed Apr. 17, 2000, now U.S. Pat. No. 6,618,916 which is a continuation of Ser. No. 08/974,677, filed Nov. 19, 1997, now U.S. Pat. No. 6,049,958, which is division of Ser. No. 08/780,437, filed Jan. 8, 1997, now U.S. Pat. No. 5,857,974.

INCORPORATION BY REFERENCE

The applicants hereby expressly incorporate by reference in their entirety the description of an "Apparatus and Method for Imaging Small Cavities" described in Proudian et al. U.S. Pat. No. 4,917,097, the description of a "Dilating and Imaging Apparatus" described in Eberle et al. U.S. Pat. No. 5,167,233, the description of an "Ultrasound Catheter" described in Eberle et al. U.S. Pat. No. 5,368,037, the description of an "Apparatus And Method For Detecting Blood Flow In Intravascular Ultrasonic Imaging" in O'Donnell et al. U.S. Pat. No. 5,453,575, and the description of a "High Resolution Intravascular Ultrasound Transducer Having a Flexible Substrate" in Eberle et al. U.S. Ser. No. 08/712,576 filed on Sep. 13, 1996 which is a continuation of U.S. Ser. No. 08/578,226 filed on Dec. 26, 1995.

FIELD OF THE INVENTION

This invention relates to ultrasound imaging apparatuses placed within a cavity to provide images thereof of the type described in Proudian et al. U.S. Pat. No. 4,917,097 and more specifically, to ultrasound imaging apparatuses and methods for fabricating such devices on a scale such that the transducer assembly portion of the imaging apparatus may be placed within a vasculature in order to produce images of the vasculature.

BACKGROUND OF THE INVENTION

In the United States and many other countries, heart disease is a leading cause of death and disability. One particular kind of heart disease is atherosclerosis, which involves the degeneration of the walls and lumen of the arteries throughout the body. Scientific studies have demonstrated the thickening of an arterial wall and eventual encroachment of the tissue into the lumen as fatty material builds upon the vessel walls. The fatty material is known as "plaque." As the plaque builds up and the lumen narrows, blood flow is restricted. If the artery narrows too much, or if a blood clot forms at an injured plaque site (lesion), flow is severely reduced, or cut off and consequently the muscle that it supports may be injured or die due to a lack of oxygen. Atherosclerosis can occur throughout the human body, but it is most life threatening when it involves the coronary arteries which supply oxygen to the heart. If blood flow to the heart is significantly reduced or cut off, a myocardial infarction or "heart attack" often occurs. If not treated in sufficient time, a heart attack often leads to death.

The medical profession relies upon a wide variety of tools to treat coronary disease, ranging from drugs to open heart "bypass" surgery. Often, a lesion can be diagnosed and treated with minimal intervention through the use of catheter-based tools that are threaded into the coronary arteries via the femoral artery in the groin. For example, one treatment for lesions is a procedure known as percutaneous transluminal coronary angioplasty (PTCA) whereby a catheter with an expandable balloon at its tip is threaded into the lesion and inflated. The underlying lesion is re-shaped, and hopefully, the lumen diameter is increased to improve blood flow.

In recent years, a new technique has been developed for obtaining information about coronary vessels and to view the effects of therapy on the form and structure of a site within a vessel rather then merely determining that blood is flowing through a vessel. The new technique, known as Intracoronary/Intravascular Ultrasound (ICUS/IVUS), employs very small transducers arranged on the end of a catheter which provide electronic transduced echo signals to an external imaging system in order to produce a two or three-dimensional image of the lumen, the arterial tissue, and tissue surrounding the artery. These images are generated in substantially real time and provide images of superior quality to the known x-ray imaging methods and apparatuses. Imaging techniques have been developed to obtain detailed images of vessels and the blood flowing through them. An example of such a method is the flow imaging method and apparatus described in O'Donnell et al. U.S. Pat. No. 5,453,575, the teachings of which are expressly incorporated in their entirety herein by reference. Other imaging methods and intravascular ultrasound imaging applications would also benefit from enhanced image resolution.

Transducer backing materials having relatively low acoustic impedance improve signal quality in transducer assemblies comprising PZT or PZT composites. The advantages of such backing materials are explained in Eberle et al. U.S. Pat. No. 5,368,037 the teachings of which are expressly incorporated in their entirety herein by reference. It is also important to select a matching layer for maximizing the acoustic performance of the PZT transducers by minimizing echoes arising from the ultrasound assembly/blood-tissue interface.

When designing a very small device for manufacture in large quantities it is important to take into consideration practical limitations such as manufacturability, reliability, resiliency and performance. The ultrasound catheter assembly must produce high quality raw image signals for the signal processing system located outside the body within which the intravascular ultrasound transducer assembly is inserted for imaging. However, there is an interest in limiting the number of parts since added complexity can increase the manufacturing costs and reduce the yield of the intravascular ultrasound catheter assemblies. The devices must be sufficiently resilient to withstand handling during manufacture and use.

SUMMARY OF THE INVENTION

It is a general object of the present invention to improve the manufacturability of an intravascular ultrasound transducer assembly.

It is another object of the present invention to decrease the per-unit cost for manufacturing ultrasound transducer assemblies.

If is yet another object of the present invention to increase the yield of manufactured ultrasound transducer assemblies.

It is a related object to provide enhanced structural integrity of the electrical connections in the transducer assembly.

It is another object of the present invention to decrease the complexity of the ultrasound transducer assembly.

The above mentioned and other objects are met in a new ultrasound transducer assembly, and method for fabricating the ultrasound transducer assembly including a PZT substrate with metallic contacts formed directly or the PZT substrate during a pre-fabrication step.

The ultrasound transducer assembly of the present invention includes a flexible substrate having an inner surface to which transducer signal lines and a ground line are attached to form a flexible circuit. In a preferred embodiment of the present invention, the flexible substrate provides the quarter-wave matching layer for the ultrasound transducers.

An ultrasound transducer array and integrated circuitry are attached during fabrication of the ultrasound transducer assembly while the flexible substrate is substantially planar (i.e., flat). In accordance with an aspect of the present invention, the signal electrode and ground electrode for transducer elements at least partially extend to the surface of the transducer elements that establishes contact with the inner surface plane of the flexible circuit. As a consequence both the ground and signal electrodes can establish direct electrical contact with corresponding signal and ground pads on the flexible surface. Therefore, conductive bridges between flexible circuit lines and electrodes located on a physically remote surface of the transducer elements are no longer required.

In a particular embodiment of the invention, after the transducer array and integrated circuit chips are attached to the flexible substrate, the flexible substrate is reshaped into a substantially non-planar shape around a lumen tube to form a substantially cylindrical shape. In accordance with another, more particular, aspect of the present invention, the spaces within the ultrasound transducer assembly between the lumen tube, the flex circuit, the transducer array and the integrated circuits are all filled with a backing material characterized by relatively low acoustic impedance. While the use of backing material in the area of the integrated circuits may reduce the physical rigidity of the ultrasound transducer assembly, in accordance with yet another aspect of the present invention, metal discs are placed upon the lumen tube of the assembly and enhance the physical integrity of the device. The metal discs also form part of a path from a ground wire to the ground electrodes of the ultrasound transducer array elements.

The integrated circuitry is housed within integrated circuit chips on the ultrasound transducer assembly. The integrated circuitry is coupled via a cable to an imaging computer which controls the transmission of ultrasound emission signals transmitted by the integrated circuitry to the ultrasound transducer array elements. The imaging computer also constructs images from electrical signals transmitted from the integrated circuitry corresponding to ultrasound echoes received by the transducer array elements.

The above described new ultrasound transducer assembly and method for making such a device retains a two-dimensional aspect to the early stages of ultrasound transducer assembly fabrication which will ultimately yield a three-dimensional, cylindrical device. Furthermore, the flexible circuit and method for fabricating an ultrasound transducer assembly according to the present invention facilitate the construction of individual, physically separate transducer elements in a transducer array. Finally, the present device eliminates a number of structures which contributed to the complexity of the ultrasound transducer assembly and the method for making such a device.

BRIEF DESCRIPTION OF THE DRAWINGS

The appended claims set forth the features of the present invention with particularity. The invention, together with its objects and advantages, may be best understood from the following detailed description taken in conjunction with the accompanying drawings of which:

FIG. 5 is a longitudinal cross-section view of the ultrasound transducer assembly illustrated in FIG. 2 sectioned along line 5—5 and running along the length of the ultrasound transducer assembly;

FIG. 5a is an enlarged view of the outer layers of the sectioned view of the ultrasound transducer assembly illustratively depicted in FIG. 5;

FIG. 6 is an enlarged and more detailed view of the transducer region of the ultrasound transducer assembly illustratively depicted in FIG. 5;

DETAILED DESCRIPTION OF THE DRAWINGS

Figure 1:
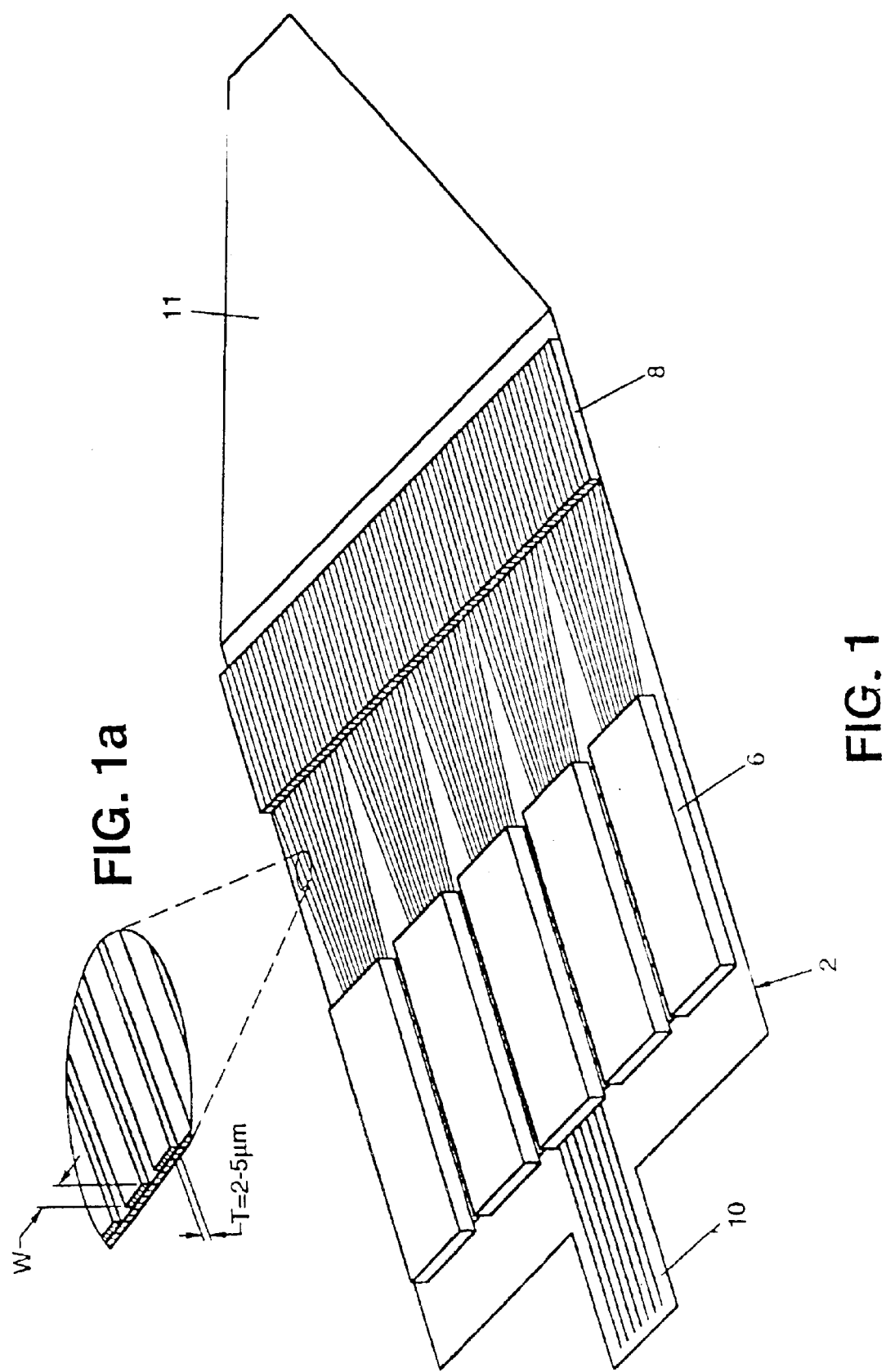
FIG. 1 is a perspective view of the flat subassembly of an ultrasound transducer assembly incorporating a 64 element ultrasound transducer array and integrated circuits mounted to a flexible circuit.

Turning now to FIG. 1, an ultrasound transducer assembly is illustratively depicted in its flat form in which it is assembled prior to forming the device into its final, cylindrical form. The ultrasound transducer assembly comprises a flex circuit 2, to which the other illustrated components of the ultrasound transducer assembly are attached. The flex circuit 2 preferably comprises a flexible polyimide film layer (substrate) such as KAPTON™ by DuPont. However, other suitable flexible and relatively strong materials, such as MYLAR (Registered trademark of E.I. DuPont) may comprise the film layer of the flex circuit 2. The flex circuit 2 further comprises metallic interconnection circuitry formed from a malleable metal (such as gold) deposited by means of known sputtering, plating and etching techniques employed in the fabrication of microelectronic circuits upon a chromium adhesion layer on a surface of the flex circuit 2.

The interconnection circuitry comprises conductor lines deposited upon the surface of the flex circuit 2 between a set of five (5) integrated circuit chips 6 and a set of sixty-four (64) transducer elements 8 made from PZT or PZT composites; between adjacent ones of the five (5) integrated circuit chips; and between the five (5) integrated circuit chips and a set of cable pads 10 for communicatively coupling the ultrasound catheter to an image signal processor via a cable (not shown). The cable comprises, for example, seven (7) 43 AWG insulated magnet wires, spirally cabled and jacketed within a thin plastic sleeve. The connection of these seven cables to the integrated circuit chips 6 and their function are explained in Proudian (deceased) et al. U.S. Pat. No. 4,917,097.

The width "W" of the individual conductor lines of the metallic circuitry (on the order of one-thousandth of an inch) is relatively thin in comparison to the typical width of metallic circuitry deposited upon a film or other flexible substrate. On the other hand, the width of the individual conductor lines is relatively large in comparison to the width of transmission lines in a typical integrated circuit. The layer thickness "T" of the conductor lines between the chips 6 and the transducer elements 8 is preferably 2–5 $\mu$m. This selected magnitude for the thickness and the width of the conductor lines enables the conductor lines to be sufficiently conductive while maintaining relative flexibility and resiliency so that the conductor lines do not break during re-shaping of the flex circuit 2 into a cylindrical shape.

The thickness of the flex circuit 2 substrate is preferably on the order of 12.5 $\mu$m to 25.0 $\mu$m. However, the thickness of the substrate is generally related to the degree of curvature in the final assembled transducer assembly and its acoustic performance. The thin substrate of the flex circuit 2, as well as the relative flexibility of the substrate material, enables the flex circuit 2 to be wrapped into a generally cylindrical shape after the integrated circuit chips 6 and the transducer elements 8 have been mounted and formed and then attached to the metallic conductors of the flex circuit 2. Therefore, in other configurations, designs, and applications requiring less or more substrate flexibility such as, for example, the various embodiments shown in Eberle et al. U.S. Pat. No. 5,368,037, the substrate thickness may be either greater or smaller than the above mentioned range. Thus, a flexible substrate thickness may be on the order of several (e.g. 5) microns to well over 100 microns (or even greater)—depending upon the flexibility requirements of the particular transducer assembly configuration.

The flex circuit is typically formed into a very small cylindrical shape in order to accommodate the space limitations of blood vessels. In such instances the range of diameters for the cylindrically shaped ultrasound transducer assembly is typically within the range of 0.5 mm. to 3.0 mm. in an ultrasound catheter for blood vessel imaging. Furthermore, the flex circuit 2 may also be incorporated into larger cylindrical transducer assemblies or even transducer assemblies having alternative shapes including planar transducer assemblies where the flexibility requirements imposed upon the flex circuit 2 are significantly relaxed. A production source of the flex circuit 2 in accordance with the present invention is Metrigraphics Corporation, 80 Concord Street, Wilmington, Mass. 01887.

The integrated circuit chips 6 are preferably of a type described in the Proudian et al. U.S. Pat. No. 4,917,097 (incorporated herein by reference) and include the modifications to the integrated circuits described in the O'Donnell et al. U.S. Pat. No. 5,453,575 (also incorporated herein by reference). However, both simpler and more complex integrated circuits may be attached to the flex circuit 2 embodying the present invention. Furthermore, the integrated circuit arrangement illustrated in FIG. 1 is intended to be illustrative. Thus, the present invention may be incorporated into a very wide variety of integrated circuit designs and arrangements contemplated to fall within the scope of the invention.

Finally, the flex circuit 2 illustratively depicted in FIG. 1 includes a tapered lead portion 11. As will be explained further below, this portion of the flex circuit 2 provides a lead into a TEFLON (registered trademark of E. I. DuPont) mold when the flex circuit 2 and attached components are re-shaped into a cylindrical shape. Thereafter, the lead portion 11 is cut from the re-shaped flex circuit 2.

Figure 2:
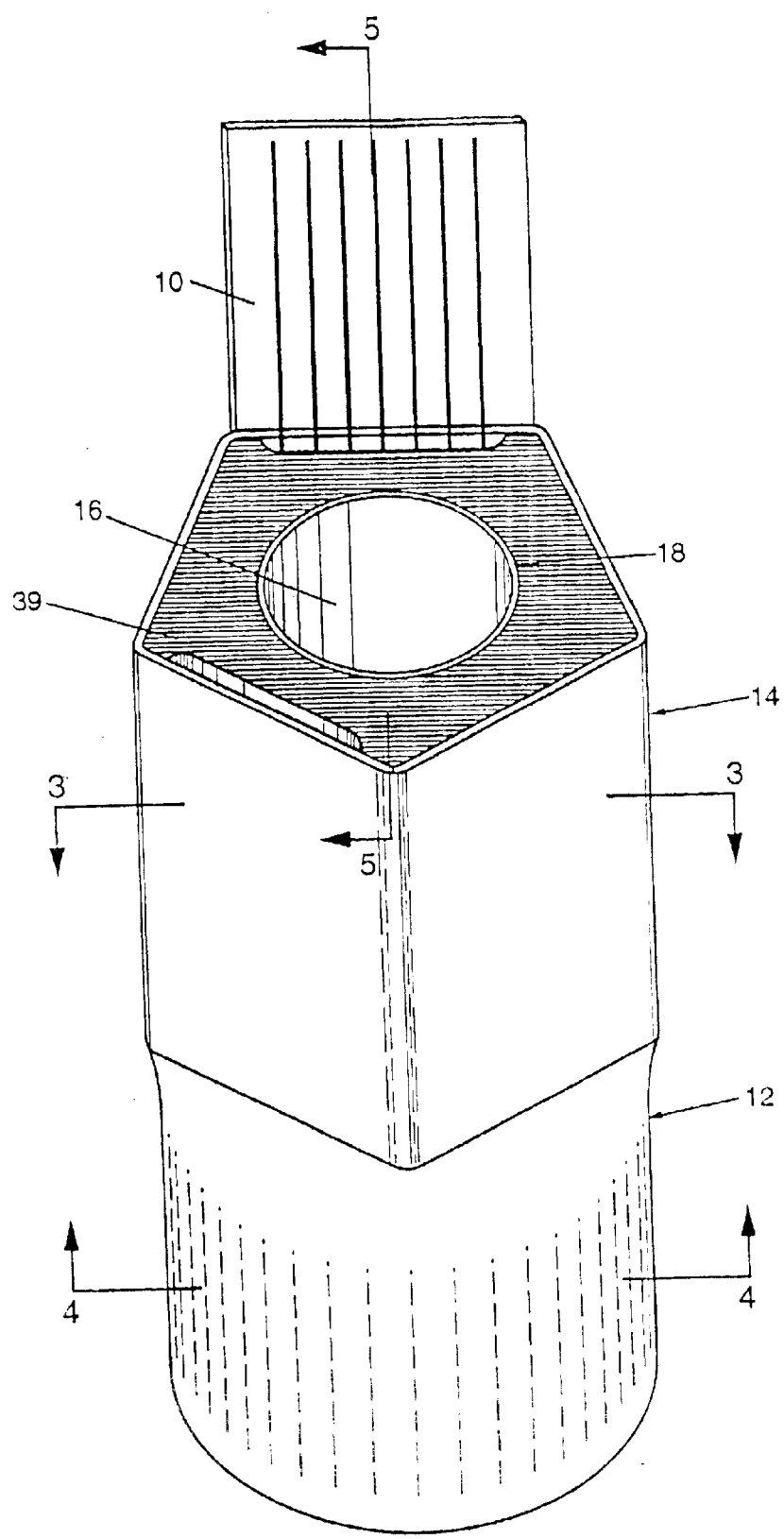
FIG. 2 is a schematic perspective view of the assembled ultrasound transducer assembly from the end containing the cable attachment pad.

Turning to FIG. 2, an illustrative ultrasound transducer assembly is shown in a re-shaped state. This shape is generally obtained by wrapping the flat, partially assembled ultrasound transducer assembly shown in FIG. 1 into a cylindrical shape by means of a molding process described below. A transducer portion 12 of the ultrasound transducer assembly containing the transducer elements 8 is shaped in a cylinder for transmitting and receiving ultrasound waves in a generally radial direction in a side-looking cylindrical transducer array arrangement. The transducer portion 12 on which the transducer elements 8 are placed may alternatively be shaped or oriented in a manner different from the cylinder illustratively depicted in FIG. 2 in accordance with alternative fields of view such as side-fire planar arrays and forward looking planar or curved arrays.

An electronics portion 14 of the ultrasound transducer assembly is not constrained to any particular shape. However, in the illustrative example the portions of the flex circuit 2 supporting the integrated circuit chips 6 are relatively flat as a result of the electrical connections between the flex circuit 2 and the integrated circuit chips 6. Thus the portion of the flex circuit 2 carrying five (5) integrated circuit chips 6 has a pentagon cross-section when re-shaped (wrapped) into a cylinder. In an alternative embodiment of the present invention, a re-shaped flex circuit having four (4) integrated circuits has a rectangular cross-section. Other numbers of integrated circuits and resulting cross-sectional shapes are also contemplated.

FIG. 2 also shows the set of cable pads 10 on the flex circuit 2 extending from the portion of the flex circuit 2 supporting the integrated circuit chips 6. A lumen 16 in the center of the ultrasound transducer assembly (within which a guidewire is threaded during the use of a catheter upon which the transducer assembly has been mounted) is defined by a lumen tube 18 made of a thin radiopaque, conductive material such as Platinum/Iridium. The radiopaque material assists in locating the ultrasound transducer assembly within the body during a medical procedure incorporating the use of the ultrasound transducer assembly. As will be explained further below, the conductive property of the lumen tube 18 offers a means for connecting the transducer ground electrodes to a ground wire included in at least one of the wires connected to the cable pads 10.

Spaces in the re-formed ultrasound transducer assembly between the integrated circuit chips 6, the transducer elements 8 and the lumen tube 18 are filled with a backing material 30. In contrast to earlier ultrasound catheter assembly designs including a relatively hard carrier material such as a rigid encapsulating epoxy, the backing material 30 that fills the spaces between the lumen tube 18 and the integrated circuit chips 6 is relatively soft. This ensures proper acoustic performance in the transducer portion 12 of the ultrasound transducer assembly. While the backing material 30 does not exhibit the rigidity of the previously used epoxy, other structures (disks) incorporated into the new transducer assembly design, described herein below, provide additional structural support for the integrated circuit chips 6 and reduces manufacturing complexity.

Figure 3:
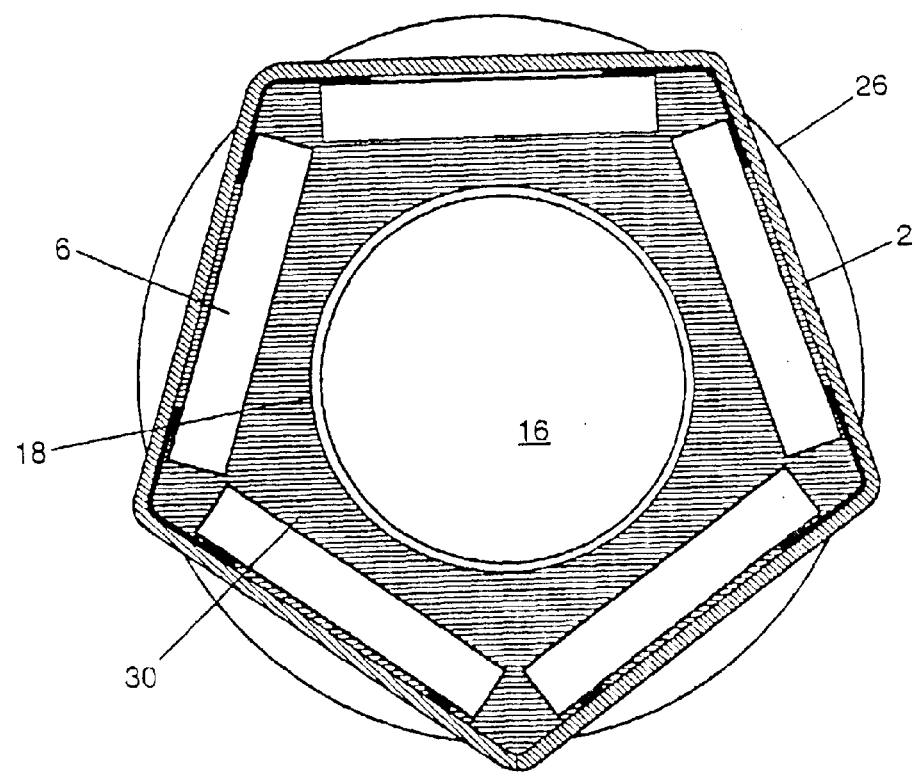
FIG. 3 is a cross-section view of the ultrasound transducer assembly illustrated in FIG. 2 sectioned along line 3—3 in the integrated circuit portion of the ultrasound transducer assembly.

Turning now to FIG. 3, a cross-section view is provided of the ultrasound transducer assembly taken along line 3—3 and looking toward the transducer portion 12 in FIG. 2. The outside of the electronics portion 14 has a pentagon shape. The circular outline 26 represents the outside of the transducer portion 12. The flex circuit 2 encompasses the cylindrically shaped ultrasound transducer assembly. The backing material 30 fills the spaces between the integrated circuit chips 6 and the lumen tube 18. While relatively soft, the backing material 30 provides a satisfactory measure of structural support to the integrated circuit chips 6 in the final assembly of the ultrasound transducer assembly. A disk (not shown in FIG. 3) inserted in one end of the ultrasound transducer assembly housing the integrated circuits 6 further enhances the structural integrity of the ultrasound transducer assembly.

Figure 4:
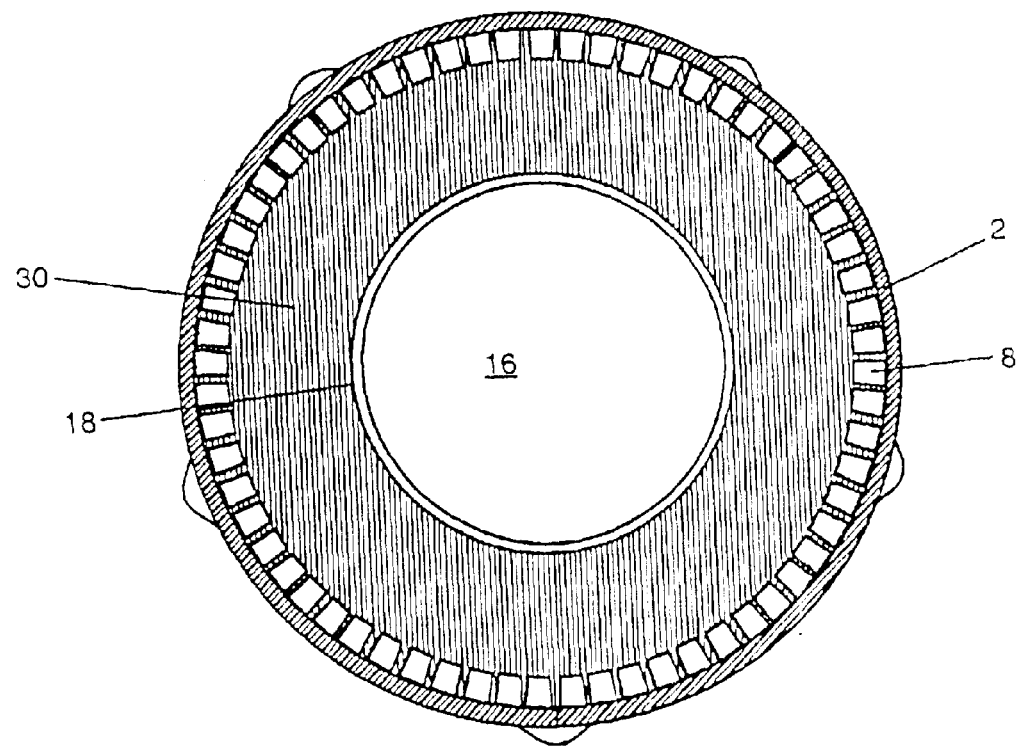
FIG. 4 is a cross-section view of the ultrasound transducer assembly illustrated in FIG. 2 sectioned along line 4—4 in the transducer portion of the ultrasound transducer assembly.

Turning now to FIG. 4, a view is provided of a cross-section of the ultrasound transducer assembly taken along line 4—4 and looking toward the electronics portion 14 in FIG. 2. The five corners of the pentagon outline comprising the electronics portion 14 are illustrated in the background of the cross-sectional view at line 4—4. The set of sixty-four (64) transducer elements 8 are displayed in the foreground of this cross-sectional view of the transducer portion 12 of the ultrasound transducer assembly. The backing material 30, characterized by relatively low acoustic impedance, fills the space between the lumen tube 18 and the transducer elements 8 as well as the gaps between adjacent ones of the sixty-four (64) transducer elements 8.

The determination of desirable materials for the backing material 30 is influenced by a number of considerations. The backing material 30 preferably possesses the ability to highly attenuate ultrasound energy emitted by the transducer elements 8. The backing material 30 also provides sufficient support for maintaining the array of transducer elements 8 in their desired configuration. A suitable material for the backing material 30 cures in a sufficiently short period of time to meet manufacturing needs. A number of known materials meeting the above described criteria for a good backing material will be known to those skilled in the art. An example of such a preferred backing material comprises a mixture of epoxy, hardener and phenolic microballoons providing high ultrasound signal attenuation and satisfactory support for the ultrasound transducer assembly.

Having generally described an ultrasound transducer assembly incorporating the flex circuit in accordance with the present invention, the advantages provided by the flex circuit will now be described in conjunction with the illustrative embodiment. The flex circuit 2 provides a number of advantages over prior ultrasound transducer assembly designs. The KAPTON substrate of the flex circuit 2 provides acoustic (quarter-wave) matching for the PZT transducer elements 8.

The ease with which the flex circuit 2 may be reshaped facilitates mounting, formation and connection of the integrated circuit chips 6 and transducer elements 8 while the flex circuit 2 is flat, and then re-shaping the flex circuit 2 into its final state after the components have been mounted, formed and connected. The flex circuit 2 is held within a frame for improved handling and positioning while the PZT and integrated circuits are bonded to complete the circuits. The single sheet of PZT or PZT composite transducer material is diced into sixty-four (64) discrete transducer elements by sawing or other known cutting methods. After dicing the transducer sheet, kerfs exist between adjacent transducer elements while the flex circuit 2 is in the flat state. After the integrated circuit chips 6 and transducer elements 8 have been mounted, formed and connected, the flex circuit 2 is re-shaped into its final, cylindrical shape by drawing the flex circuit 2 and the mounted elements into a TEFLON mold (described further below).

Also, because the integrated circuits and transducer elements of the ultrasound transducer assembly may be assembled while the flex circuit 2 is in the flat state, the flex circuit 2 may be manufactured by batch processing techniques wherein transducer assemblies are assembled side-by-side in a multiple-stage assembly process. The flat, partially assembled transducer assemblies are then re-shaped and fabrication completed.

Furthermore, it is also possible to incorporate strain relief in the catheter assembly at the set of cable pads 10. The strain relief involves flexing of the catheter at the cable pads 10. Such flexing improves the durability and the positionability of the assembled ultrasound catheter within a patient.

Another important advantage provided by the flex circuit 2, is the relatively greater amount of surface area provided in which to lay out connection circuitry between the integrated circuit chips 6 and the transducer elements 8. In the illustrated embodiment of the present invention, the transducer array includes sixty-four (64) individual transducer elements. This is twice the number of transducer elements of the transducer array described in the Proudian '097 patent. Doubling the number of transducer elements without increasing the circumference of the cylindrical transducer array doubles the density of the transducer elements. If the same circuit layout described in the Proudian '097 was employed for connecting the electronic components in the sixty-four (64) transducer element design, then the density of the connection circuitry between the integrated circuit chips 6 and the transducer elements 8 must be doubled.

However, the flex circuit 2 occupies a relatively outer circumference of: (1) the transducer portion 12 in comparison to the transducer elements 8 and, (2) the electronics portion 14 in comparison to the integrated circuit chips 6. The relatively outer circumference provides substantially more area in which to lay out the connection circuitry for the sixty-four (64) transducer element design in comparison to the area in which to lay out the connection circuitry in the design illustratively depicted in the Proudian '097 patent. As a result, even though the number of conductor lines between the integrated circuit chips 6 and the transducer elements 8 doubles, the density of the conductor lines is increased by only about fifty percent (50%) in comparison to the previous carrier design disclosed in the Proudian '097 patent having a substantially same transducer assembly diameter.

Yet another advantage provided by the flex circuit 2 of the present invention is that the interconnection solder bumps, connecting the metallic pads of the integrated circuit chips 6 to matching pads on the flex circuit 2, are distributed over more of the chip surface, so the solder bumps only have to be slightly smaller than the previous design having only thirty-two (32) transducer elements.

The integrated circuit chips 6 are preferably bonded to the flex circuit 2 using known infrared alignment and heating methods. However, since the flex circuit 2 can be translucent, it is also possible to perform alignment with less expensive optical methods which include viewing the alignment of the integrated circuit chips 6 with the connection circuitry deposited upon the substrate of the flex circuit 2 from the side of the flex circuit 2 opposite the surface to which the integrated circuit chips 6 are to be bonded.

Turning now to FIGS. 5 and 5a, a cross-sectional view and enlarged partial cross-sectional view are provided of the ultrasound transducer assembly illustrated in FIG. 2 sectioned along line 5—5 and running along the length of the ultrasound transducer assembly embodying the present invention. A KAPTON substrate 33 portion of the flex circuit 2, approximately 13 $\mu$m in thickness, completely surrounds the ultrasound transducer assembly, acts as an acoustic matching layer and protects the electronic components of the ultrasound transducer assembly. Metallic transducer signal lines 34, approximately 2–5 $\mu$m in thickness, are bonded to the KAPTON substrate 33 with a chromium adhesion layer to form the flex circuit 2.

The transducer signal lines 34 of the flex circuit 2 are illustrated as a solid layer in FIG. 5. However, it will be appreciated by those skilled in the art that the transducer signal lines 34 are fabricated from a solid layer (or layers) of deposited metal using well known metal layer selective etching techniques such as masking or selective plating techniques.

A cable 35 of the type disclosed in the Proudian '097 patent is connected to the cable pads 10 for carrying control and data signals transmitted between the ultrasound transducer assembly and a processing unit. A set of solder bumps such as solder bump 36 connect the contacts of the integrated circuit chips 6 to the transducer signal lines 34 of the flex circuit 2. Two-part epoxy 38 bonds the integrated circuit chips 6 to-the flex circuit 2.

FIG. 5 also shows the backing material 30 which fills the gaps between the integrated circuits and the lumen tube 18. The lumen tube 18 has a diameter of approximately 0.024" and is approximately 25 $\mu$m thick. The space between the transducers 8 and the lumen tube 18 in transducer portion 12 of the ultrasound transducer assembly is filled by the backing material 30 having a low acoustic impedance and therefore well suited for attenuating ringing in the ultrasound transducer assembly by absorbing ultrasound waves emitted by the transducer elements toward the lumen tube 18. The transducer portion 12 of the ultrasound transducer assembly of the present invention is described in greater detail below in conjunction with FIGS. 6 and 6a.

A pair of grounding discs 37 and 39 are located on each end of the ultrasound transducer assembly. The primary function of the discs 37 and 39 is to provide a ground contact between a ground wire on the cable 35, the lumen tube 18, and the transducer ground electrode leads. In the preferred embodiment of the present invention, mechanical contacts (rather than solder) exist between the transducer ground electrode pads and the disc 37, the disc 37 and the lumen tube 18, the lumen tube 18 and disc 39, and disc 39 and a pad on the flex circuit 2 to a ground wire in the cable 35.

Figure 7:
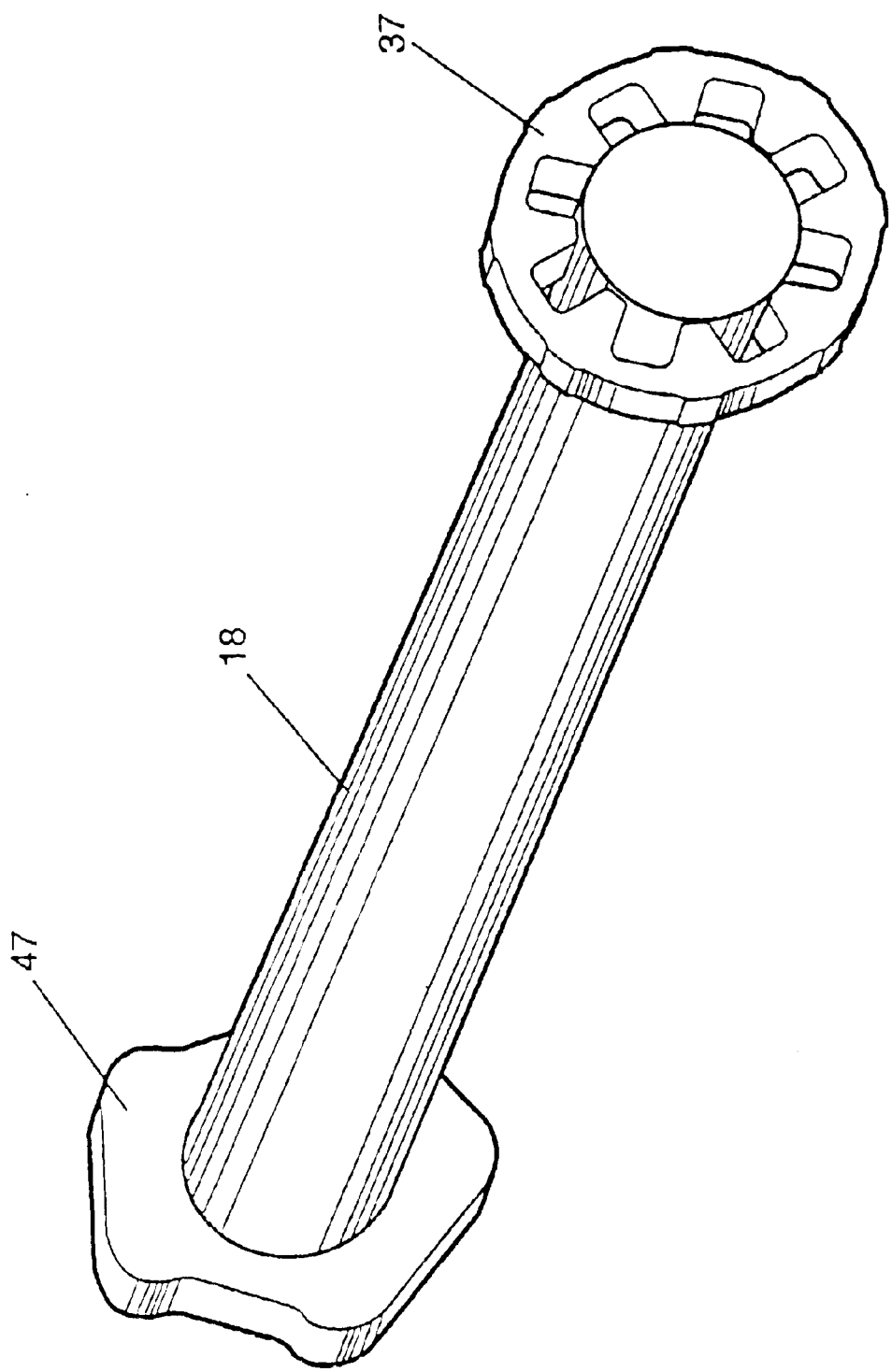
FIG. 7 is a perspective view of a lumen tube and discs assembly in accordance with a preferred embodiment of the present invention.
Figure 8:
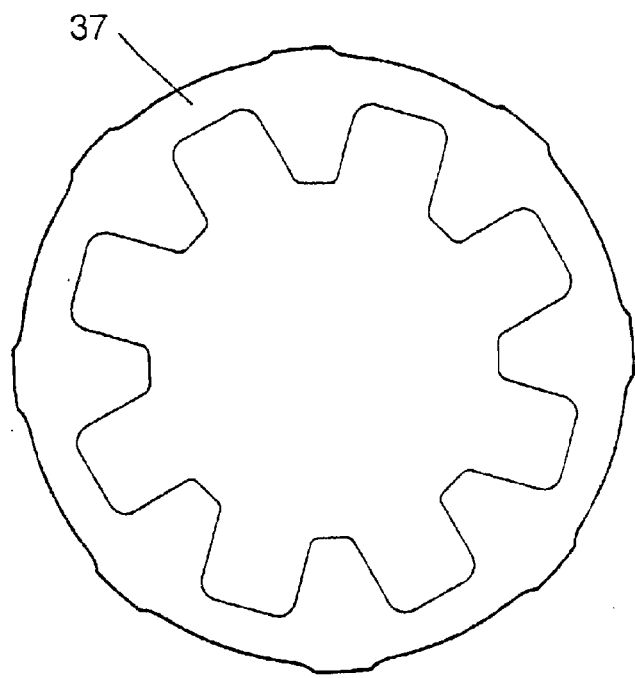
FIG. 8 is an outline of the generally circular disc which is pressed onto the lumen tube at the transducer array portion of the ultrasound transducer assembly.
Figure 9:
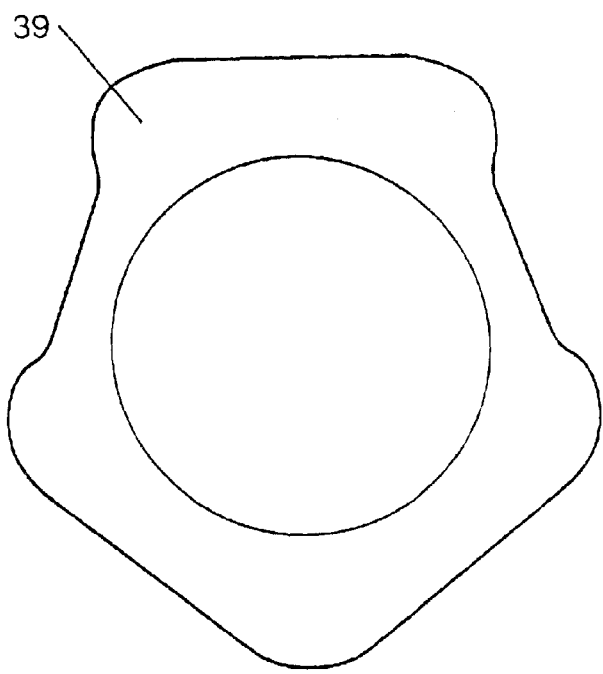
FIG. 9 is an outline of the generally pentagonal disc which is pressed onto the lumen tube at the electronics portion of the ultrasound transducer assembly.

The ground contact is established by press-fitting the discs 37 and 39 onto the lumen tube 18 as shown in FIG. 7. Thereafter, the flex circuit 2 is wrapped around the discs 37 and 39 and the resulting cylindrical device is filled with the backing material 30 in order to create a device having a cross-section illustratively depicted in FIG. 5 after final assembly. As illustratively depicted in FIGS. 8 and 9, the disc 37 is generally circular (to provide a round cylinder shape to the transducer portion 12 of the ultrasound transducer assembly), and the disk 39 is generally pentagonal (to provide a five-sided cylinder shape to accommodate the arrangement of the five (5) integrated circuit chips 6 attached to flex circuit 2 in the electronics portion 14). Furthermore, the discs 37 and 39 are formed with through holes to facilitate a step of injecting backing material into the ultrasound transducer assembly during a preferred fabrication process described herein below.

Figure 6A:
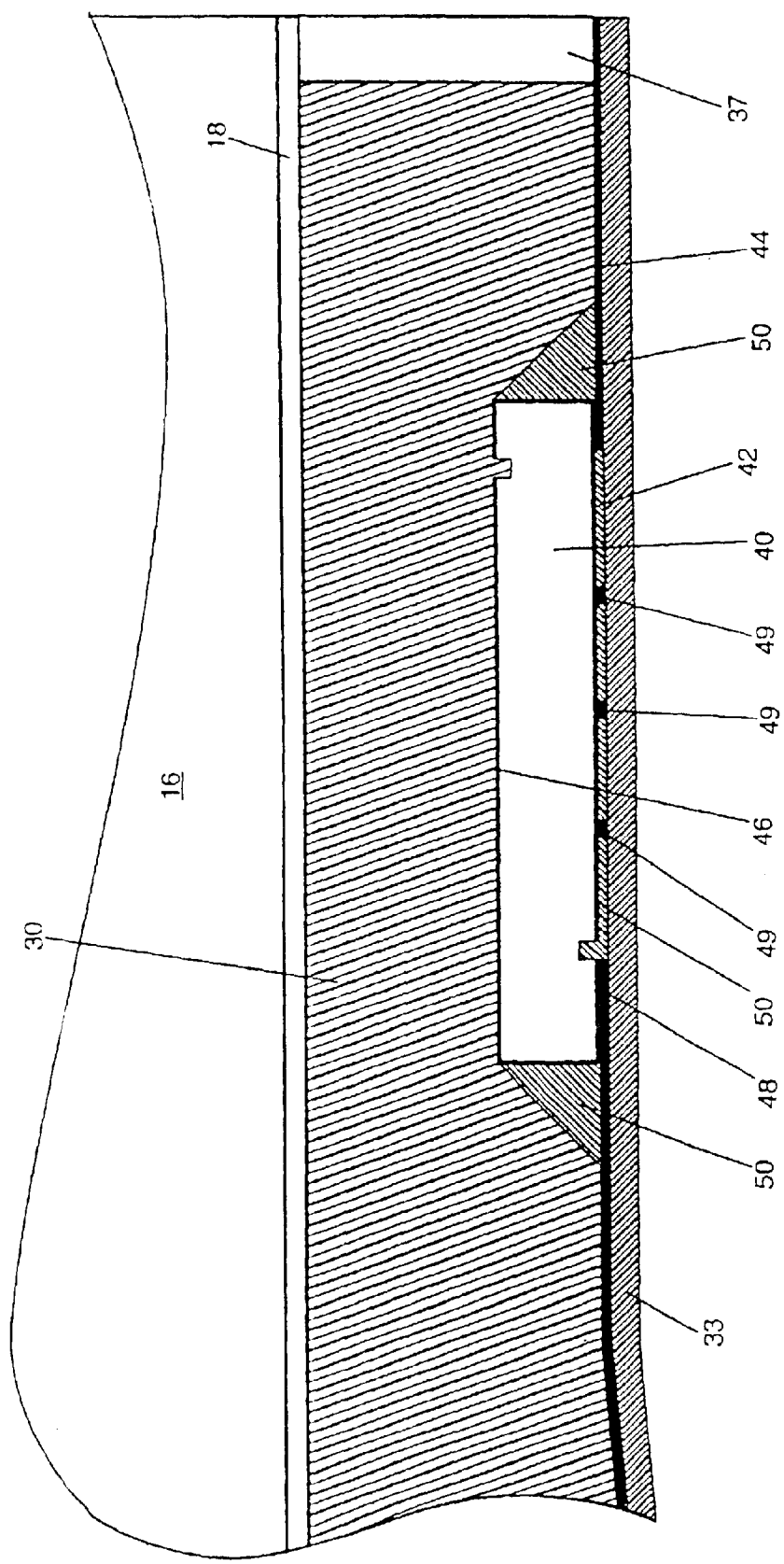
FIG. 6a is a further enlarged view of a portion of the transducer region containing a cross-sectioned transducer.
Figure 6B:
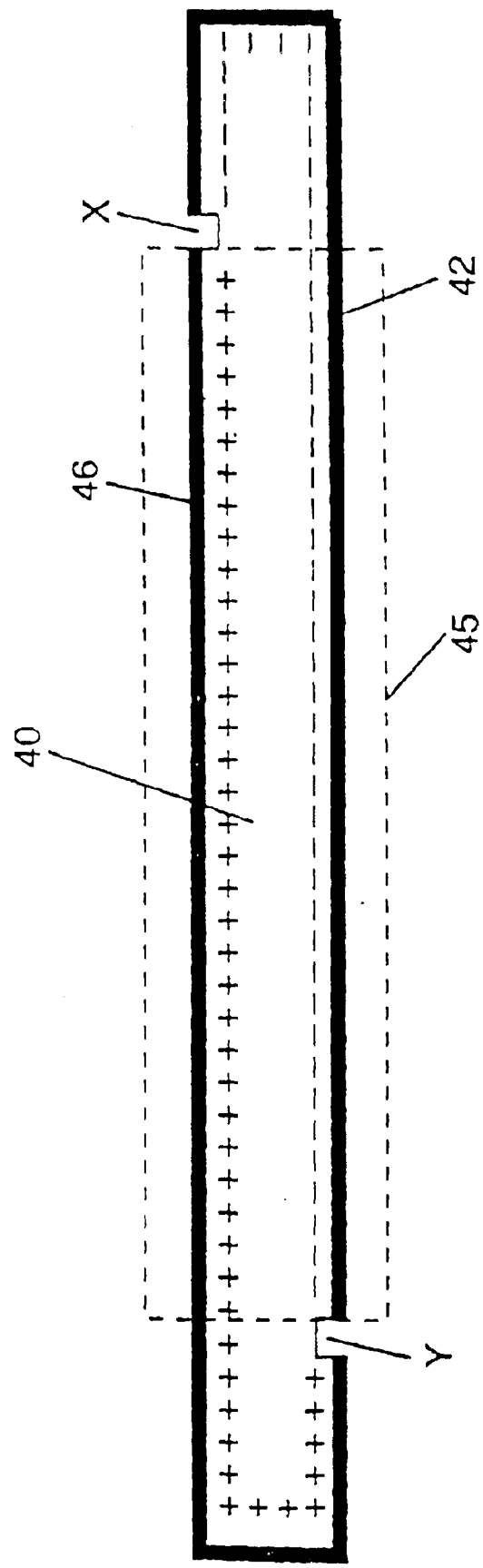
FIG. 6b is a side view of a single transducer element in accordance with a preferred embodiment of the invention.

Turning now to FIGS. 6, 6a and 6b, the transducer elements 8 comprise PZT or PZT composite 40 approximately 90 $\mu$m in thickness and, depending on frequency, approximately 40 $\mu$m wide and 700 $\mu$m long. Each transducer element includes a Cr/Au ground electrode 42 and a Cr/Au signal electrode 46 which are approximately 0.1 $\mu$m in thickness. As illustratively depicted in FIG. 6b, the electrodes are constructed by encapsulating the PZT or PZT composite 40 in Cr/Au. Thereafter, the electrodes 42 and 46 are defined as two separate metal sheets by cutting (or etching) a first groove at point X on a first surface primarily containing the signal electrode 46 and cutting a second groove at point Y on a second surface primarily containing the ground electrode 42. The grooves at points X and Y define the active region 45 of the transducers 8. The reduced active region 45, that does not include the ends of the transducer elements 8 provides edge damping and potentially improved image quality.

As illustratively depicted in FIG. 6b, the positions of the grooves X and Y establish electrical isolation between the electrodes 42 and 46 in a manner such that connections between electrical lines 44 (ground) and 34 (signal) and corresponding transducer electrodes 42 and 46 are achieved without fabricating bridges between lead lines on the flex circuit 2 and the upper surface of the transducers 8 defining the signal electrode 46. As a consequence of positioning all electrode contacts on a single plane, connections between electrodes 42 and 46, and corresponding lines 44 and 34 on the flex circuit 2 are preferably achieved by means of pressure and adhesive materials rather than soldering or conductive glues. More particularly, in a preferred embodiment, a two-part epoxy 50, approximately 2–5 $\mu$m in thickness occupies the space between the ground electrode 42 and the KAPTON substrate 33 of the flex circuit 2. The two-part epoxy 50 holds the transducer elements 8 in signal contact with the-transducer signal lines 34 of the flex circuit 2 while the relative rough surfaces of the PZT or PZT composite 40 establish several points of contact between the transducer electrodes 42 and 46, and corresponding electrical lines 44 and 34.

The thickness of the two-part epoxy 50 between the substrate 33 and the ground electrode 42 is controlled by spacer bars 49. The spacer bars 49 run the entire width of the flat flex circuit. However, the continuous spacer bar material is separated into discrete bars by a saw during the step of dicing the transducer material into discrete transducer elements 8. Additional two-part epoxy 50 is applied at the ends of the transducers 8.

Finally, it is noted that the transducer signal lines 34 are separate, electrically isolated conductors which terminate at signal contacts 48. The transducer signal lines 34 couple the transducer elements 8 to corresponding I/O channels of the integrated circuit chips 6. The ground line 44 comprises a continuous conductor is not cut through since the integrated circuits and the distal portion of the ground line 44 are fixtured at a lower elevation than the transducer array during dicing and maintains the transducer ground electrode 42 for each of the transducer elements 8 at a common electrical potential established by a ground wire within the cable 35. This ground connection is achieved through the metallic disc 37 which conducts a ground signal via the lumen tube 18 and disc 39. The disc 39 is connected directly to the ground signal which originates from the cable 35.

Figure 10:
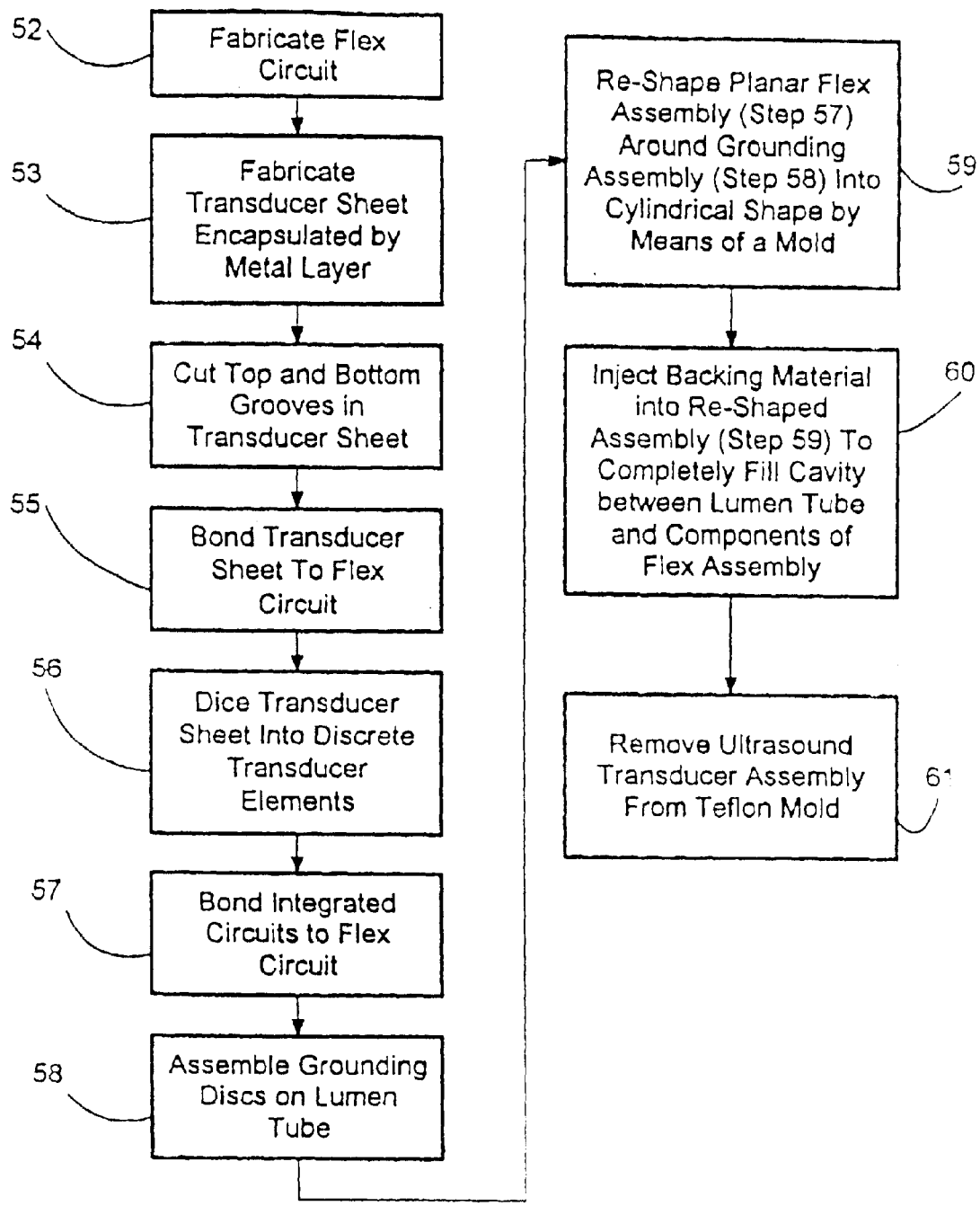
FIG. 10 is a flowchart summarizing the steps for fabricating a cylindrical ultrasound transducer assembly embodying the present invention.

Turning now to FIG. 10, the steps are summarized for fabricating the above-described ultrasound transducer assembly embodying the present invention. It will be appreciated by those skilled in the art that the steps may be modified in alternative embodiments of the invention.

At step 52, the flex circuit 2 is formed by depositing conductive materials such as Chromium/Gold (Cr/Au) on a surface of the KAPTON substrate 33. Chromium is first deposited as a thin adhesion layer, typically 50–100 Angstroms thick, followed by the gold conducting layer, typically 2–5 $\mu$m thick. Using well known etching techniques, portions of the Cr/Au layer are removed from the surface of the KAPTON substrate 33 in order to form the transducer signal lines 34, the ground line 44, and the spacer bars 49 of the flex circuit 2. Also during step 52 gold bumps, used to form the signal contacts 48, are formed on the flex circuit 2.

In a separate and independent procedure with respect to the above-described step for fabricating the flex circuit 2, at step 53 a thin metal layer, on the order of 0.1 $\mu$m to 5.0 $\mu$m is applied to a single PZT or PZT composite crystal. In contrast to an alternative metalization procedure, during step 53 the metal layer covers the top, bottom and ends of the PZT crystal. Next, during step 54, the metal layer is divided into two separate metal layers by cutting the two grooves identified previously by the X and Y in FIG. 6a. These two metal layers will later comprise the separate ground electrode 42 and signal electrode 46 for each of the transducer elements.

Next, at step 55, the metallized PZT or PZT composite 40 is bonded under pressure to the flex circuit 2 by means of two-part epoxy 50, and cured for a reasonable period. This is typically done overnight. The pressure exerted during bonding reduces the thickness of the two-part epoxy 50 to a thickness of approximately 2–5 $\mu$m, depending on the chosen thickness of the spacer bars 49 and signal contacts 48. The very thin layer of two-part epoxy 50 provides good adhesion of the metallized PZT or PZT composite to the flex circuit 2 without significantly affecting the acoustic performance of the transducer elements 8. During exertion of pressure during step 55, a portion of the two-part epoxy 50 squeezes out from between the flex circuit 2 and the transducer sheet from which the transducer elements 8 will be formed. That portion of the two-part epoxy 50 also forms a fillet at each end of the bonded transducer sheet (See FIG. 6). The fillets of the two-part epoxy 50 provide additional support for the transducer elements 8 during sawing of the PZT or PZT composite 40 into physically discrete transducer elements. Additional two-part epoxy 50 may be added around the PZT to make the fillet more uniform.

In order to obtain good performance of the elements and to facilitate re-shaping the flex circuit 2 into a cylinder after the integrated circuit chips 6 and transducer elements 8 are attached, the transducer sheet is diced to form physically discrete transducer elements 8 during step 56. Dicing is accomplished by means of a well known high precision, high speed disc sawing apparatus, such as those used for sawing silicon wafers. It is desirable to make the saw kerfs (i.e., the spaces between the adjacent transducer elements) on the order of 15–25 $\mu$m when the flex circuit is re-shaped into a cylindrical shape. Such separation dimensions are achieved by known high precision saw blades having a thickness of 10–15 $\mu$m.

Continuing with the description of the dicing step 56, after the two part epoxy 50 is fully cured, the flex circuit 2 is fixtured to facilitate dicing of the transducer sheet into sixty-four (64) discrete elements. The flex circuit 2 is fixtured by placing the flex circuit 2 onto a vacuum chuck (of well known design for precision dicing of very small objects such as semiconductor wafers) which is raised by 50–200 $\mu$m in the region of the transducer elements 8 in order to enable a saw blade to penetrate the flex circuit 2 in the region of the transducer elements a without affecting the integrated circuit region and without sawing through the distal portion of the ground line proximate to the disc 37. The saw height is carefully controlled so that the cut extends completely through the PZT or PZT composite 40 and partially into the KAPTON substrate 33 of the flex circuit 2 by a few microns. Extending the cut further into the flex circuit 2 further reduces the conduction of ultrasound to adjacent transducer elements. The resulting transducer element pitch (width) is on the order of 50 $\mu$m. In alternative embodiments this cut may extend all the way through the flex circuit 2 in order to provide full physical separation of the transducer elements.

Alternatively a laser performs the step of dicing the transducer elements. However, a drawback of using a laser to dice the transducer sheet is that the laser energy may depolarize the PZT or PZT composite 40. In view of present difficulties associated with polarization of the separated PZT transducer elements, the sawing method is presently preferred.

After the PZT or PZT composite 40 has been diced into discrete transducer elements and cleaned of dust arising from the sawing of the PZT or PZT composite 40, at step 57 the integrated circuit chips 6 are flip-chip bonded in a known manner to the flex circuit 2 using pressure and heat to melt solder bumps such as solder bump 36 forming the electrical contacts between the flex circuit 2 and the pads of the integrated circuit chips 6. The integrated circuit chips 6 are aligned by means of either infrared or visible light alignment techniques so that the Indium solder bumps on the integrated circuits 6 align with the pads on the flex circuit 2. These alignment methods are well known to those skilled in the art. The partially assembled ultrasound transducer assembly is now ready to be formed into a substantially cylindrical shape as shown in FIGS. 2, 3 and 4.

Before re-shaping the flat flex circuit 2 (as shown in FIG. 1) into a cylindrical shape around the lumen tube 18, at step 58 the grounding discs 37 and 39 are pressed onto the ends of the lumen tube 18 (see FIG. 7). The tolerances of the inner sprockets of the disc 37 and the inner diameter of the disc 39 and the outer diameter of the lumen tube 18 are such that the discs 37 and 39 frictionally engage the outer surface of the lumen tube 18. The discs 37 and 39 shown in FIGS. 8 and 9 respectively, ensure concentricity of the transducer portion 12 of the assembled ultrasound transducer device around the lumen tube 18 and facilitates even distribution of the backing material 30 within the spaces of the ultrasound transducer apparatus between the lumen tube and the ultrasound transducers 8.

Figure 11:
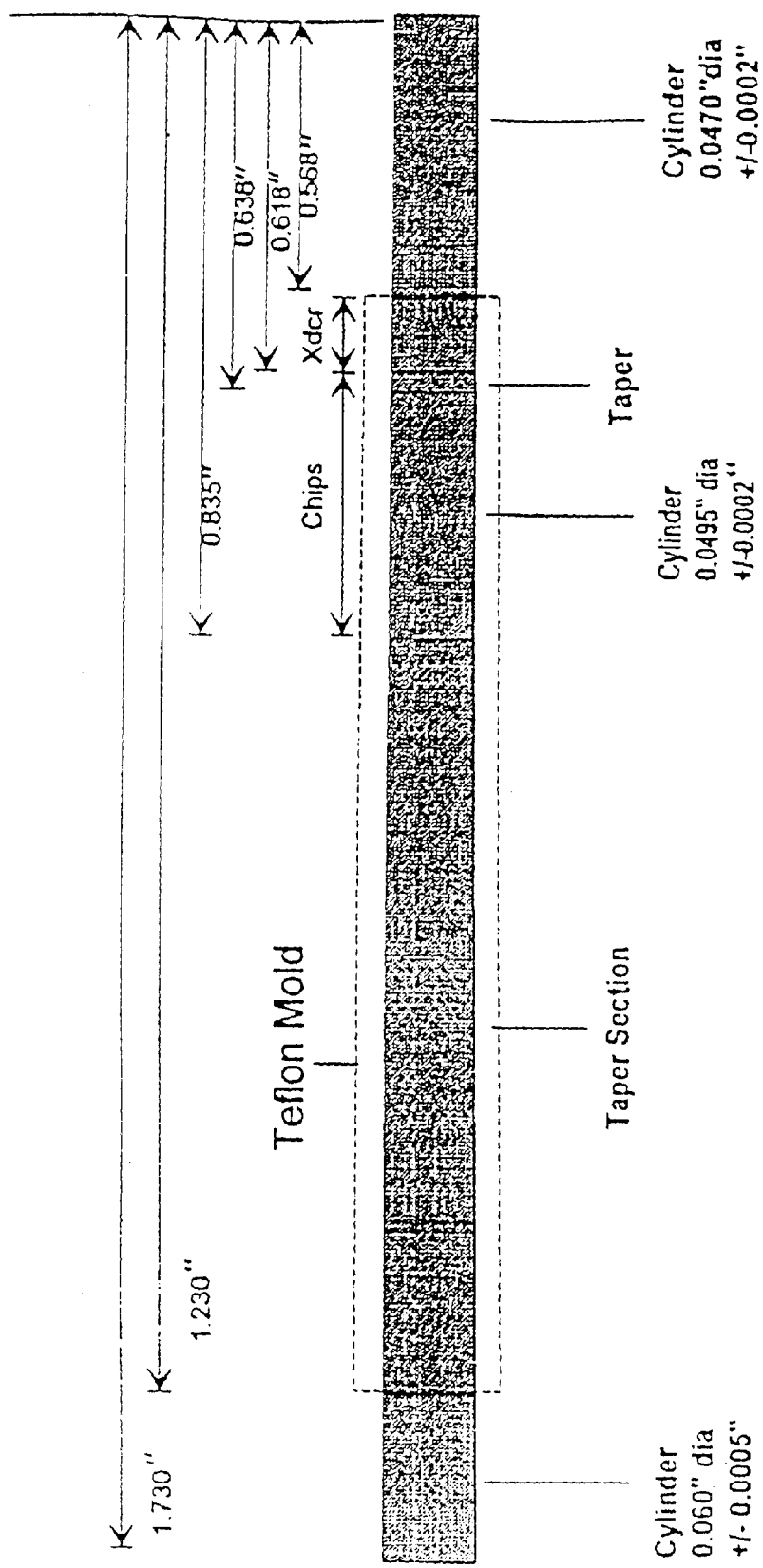
FIG. 11 is a schematic drawing showing a longitudinal cross-section view of a mandrel used to form a mold within which a partially assembled ultrasound transducer assembly is drawn in order to reshape the flat, partially assembled transducer assembly into a substantially cylindrical shape and to thereafter finish the ultrasound catheter assembly in accordance with steps 59–61 of FIG. 10.

At step 59, the grounding assembly, consisting of the lumen tube 18 and discs 37 and 39, and the partially assembled flex circuit 2, are carefully matched up and then drawn into a preformed TEFLON mold having very precise dimensions. The TEFLON mold is formed by heat shrinking TEFLON tubing over a precision machined mandrel (as shown in FIG. 11 and described below). The heat shrinkable TEFLON tubing is removed and discarded after fabrication of the ultrasound transducer assembly is complete. As a result, distortion of a mold through multiple uses of the same mold to complete fabrication of several ultrasound transducer assemblies is not a problem, and there is no clean up of the mold required.

The TEFLON molds incorporate a gentle lead-in taper enabling the sides of the flex circuit 2 to be carefully aligned, and the gap between the first and last elements to be adjusted, as the flex circuit 2 is pulled into the mold. In the region of the transducer, the mold and the disc 37 are held to a diametric precision of 2–3 $\mu$m. Since the flex circuit 2 dimensions are formed with precision optical techniques, the dimensions are repeatable to less than 1 $\mu$m, the gap between the first and last elements (on the outer edges of the flat flex circuit 2) can be repeatable and similar to the kerf width between adjacent elements.

A TEFLON bead is placed within the lumen tube 18 in order to prevent filling of the lumen 16 during the steps described below for completing fabrication of the ultrasound transducer assembly.

After drawing the flex circuit into the mold, at step 60 backing material 30 is injected into the distal end of the ultrasound transducer assembly in order to fill the kerfs between transducer elements and any gaps between the preformed portion of the backing material 30 and the transducer elements 8. The backing material is injected by means of the through holes in the grounding disc 37. The air occupying the space between the lumen tube 18 and components of the flex circuit assembly escapes through holes in the disc 39. This ensures that there are no air gaps in the region of the ultrasound transducer assembly having the transducer array since air gaps degrade the performance of the ultrasound transducer assembly and degrade the mechanical integrity of the device. In contrast to prior fabrication methods employing separate and distinct chip carrier and backing materials, the present design utilizes the backing material 30 to support the integrated circuits. This modification reduces manufacturing complexity while providing sufficient support for the integrated circuits.

At step 61, after the backing material 30 cures, the ultrasound transducer assembly is removed from the mold by either pushing the device out of the mold or carefully cutting the TEFLON mold and peeling it from the ultrasound transducer assembly. The TEFLON bead is removed from the lumen tube 18. Stray backing material is removed from the device.

Having described one method for fabricating an ultrasound transducer assembly incorporating the flex circuit 2, it is noted that the order of the steps is not necessarily important. For example, while it is preferred to attach the integrated circuits 6 to the flex circuit 2 after the transducers 6 have been bonded to the flex circuit 2, such an order for assembling the ultrasound transducer assembly is not essential. Similarly, it will be appreciated by those skilled in the art that the order of other steps in the described method for fabricating an ultrasound transducer assembly can be re-arranged without departing from the spirit of the present invention.

Turning briefly to FIG. 11, a longitudinal cross-section view is provided of the mandrel previously mentioned in connection with the description of step 59 above. The mandrel enables a TEFLON tube to be reformed into a mold (shown generally by a ghost outline) having very precise inside dimensions by heat shrinking the TEFLON tube onto the mandrel. The TEFLON mold is thereafter used to re-shape the partially assembled ultrasound transducer assembly during step 59. While precise dimensions and tolerances are provided on the drawing, they are not intended to be limiting since they are associated with a particular size and shape for an ultrasound transducer assembly embodying the present invention.

The mandrel and resulting inside surface of the TEFLON mold generally display certain characteristics. First, the mandrel incorporates a taper from a maximum diameter at the end where the flex circuit enters the mold to a minimum diameter at the portion of the mold corresponding to the transducer portion of the ultrasound transducer assembly. This first characteristic facilitates drawing the flex circuit into the mold.

Second, the mold has a region of constant diameter at the region where the integrated circuit portion will be formed during step 59. This diameter is slightly greater than the diameter of the transducer region of the mold where the diameter of the inside surface is precisely formed into a cylinder to ensure proper mating of the two sides of the flex circuit when the flat, partially assembled transducer assembly is re-shaped into a cylindrical transducer assembly. The greater diameter in the integrated circuit region accommodates the points of the pentagon cross-section created by the integrated circuit chips 6 when the flat flex circuit is re-shaped into a cylinder.

Finally, a second taper region is provided between the integrated circuit and transducer portions of the mold in order to provide a smooth transition from the differing diameters of the two portions.

Figure 12:
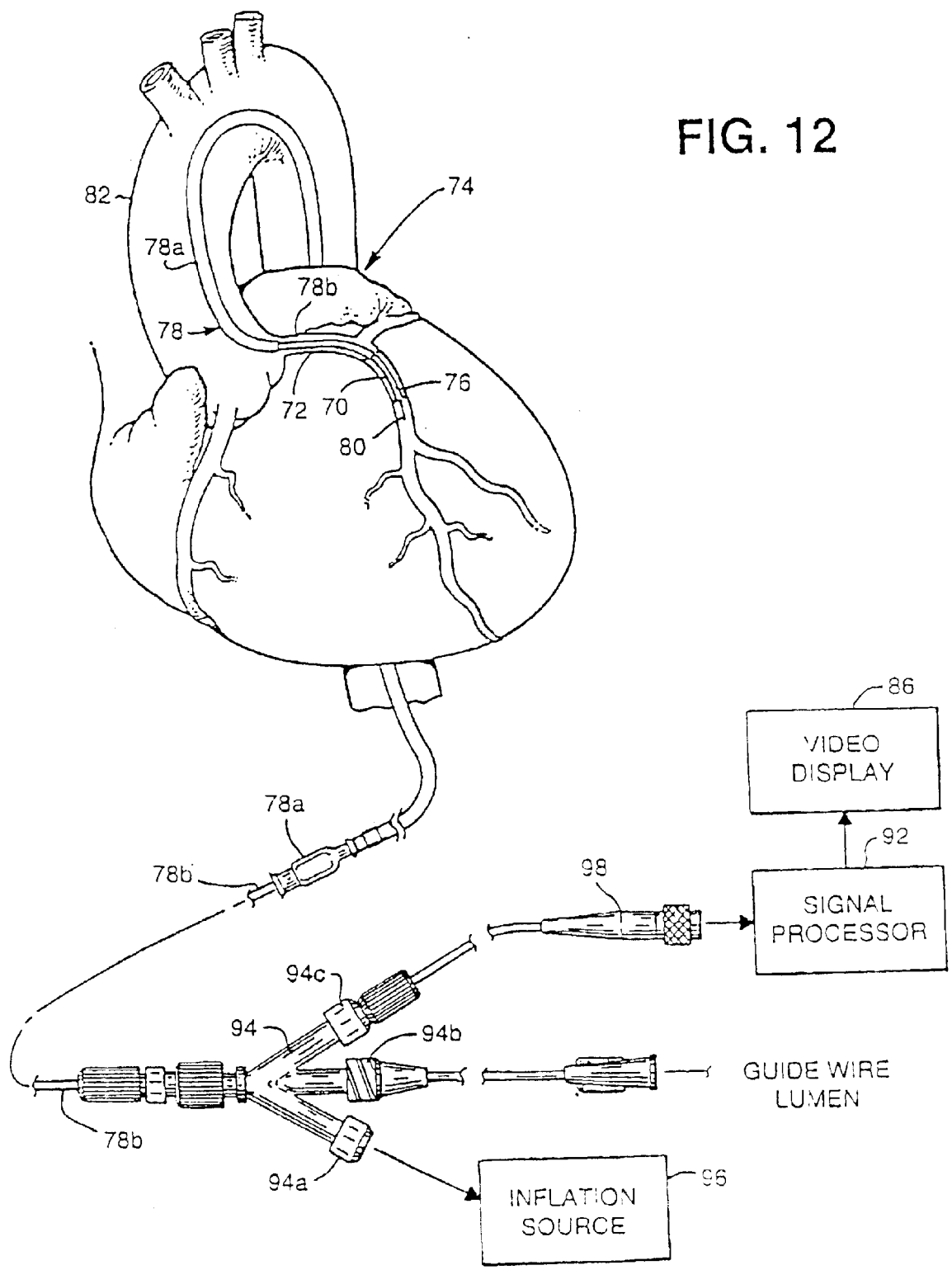
FIG. 12 is a schematic drawing of an illustrative example of an ultrasound imaging system including an ultrasound transducer assembly embodying the present invention and demonstrating the use of the device to image a coronary artery.
Figure 13:
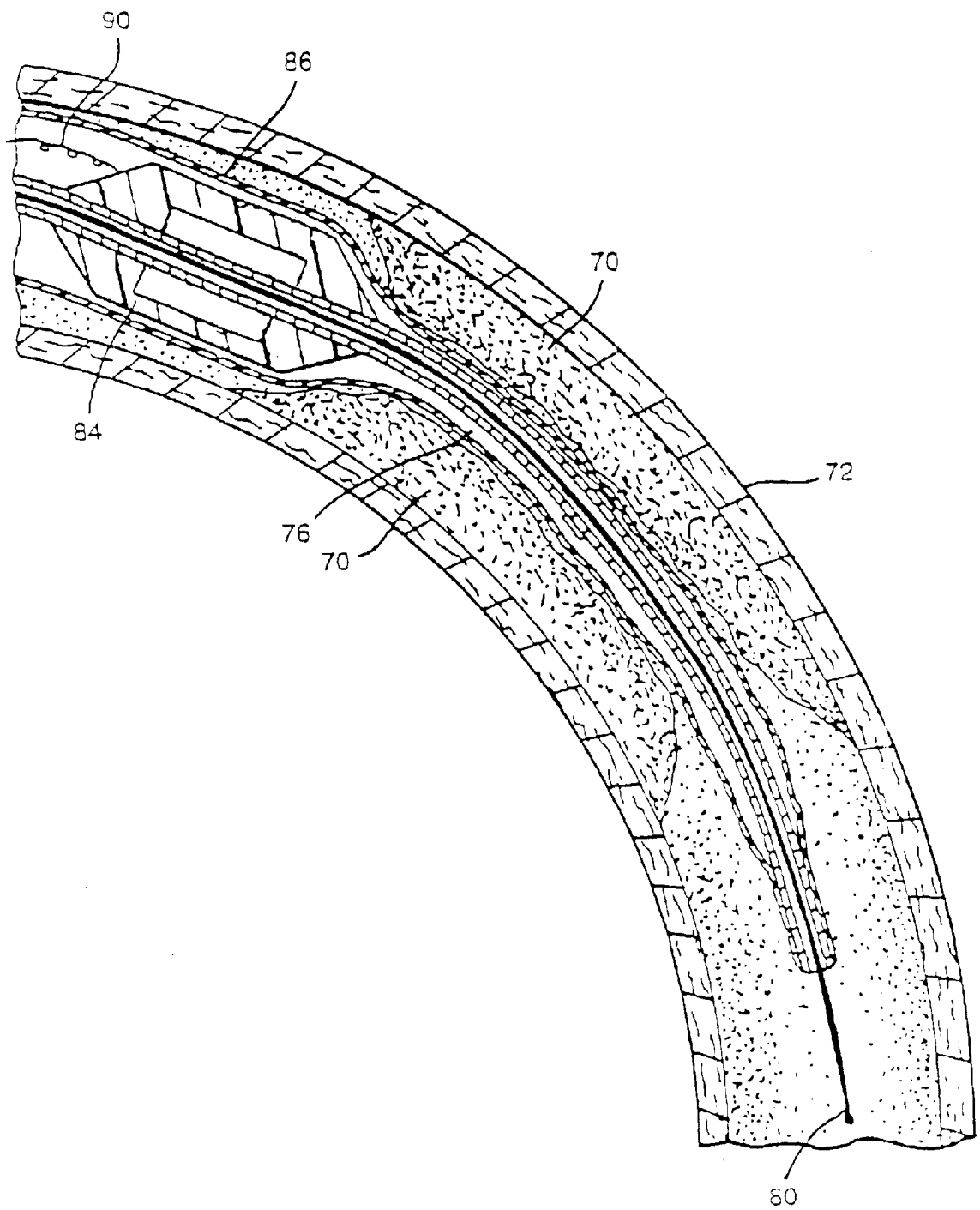
FIG. 13 is an enlarged and partially sectioned view of a portion of the coronary artery in FIG. 12 showing the ultrasound transducer assembly incorporated within an ultrasound transducer probe located in a catheter proximal to a balloon and inserted within a coronary artery.

The above description of the invention has focused primarily upon the structure, materials and steps for constructing an ultrasound transducer assembly embodying the present invention. Turning now to FIGS. 12 and 13, an illustrative example of the typical environment and application of an ultrasound device embodying the present invention is provided. Referring to FIGS. 12 and 13, a buildup of fatty material or plaque 70 in a coronary artery 72 of a heart 74 may be treated in certain situations by inserting a balloon 76, in a deflated state, into the artery via a catheter assembly 78. As illustrated in FIG. 12, the catheter assembly 78 is a three-part assembly, having a guide wire 80, a guide catheter 78a for threading through the large arteries such as the aorta 82 and a smaller diameter catheter 78b that fits inside the guide catheter 78a. After a surgeon directs the guide catheter 78a and the guide wire 80 through a large artery leading via the aorta 82 to the coronary arteries, the smaller catheter 78b is inserted. At the beginning of the coronary artery 72 that is partially blocked by the plaque 70, the guide wire 80 is first extended into the artery, followed by catheter 78b, which includes the balloon 76 at its tip.

After the balloon 76 has entered the coronary artery 72, as in FIG. 13, an ultrasonic imaging device including a probe assembly 84 housed within the proximal sleeve 86 of the balloon 76 provides a surgeon with a cross-sectional view of the artery on a video display 88. In the illustrated embodiment of the invention, the transducers emit 20 MHz ultrasound excitation waveforms. However, other suitable excitation waveform frequencies would be known to those skilled in the art. The transducers of the probe assembly 84 receive the reflected ultrasonic waveforms and convert the ultrasound echoes into echo waveforms. The amplified echo waveforms from the probe assembly 84, indicative of reflected ultrasonic waves, are transferred along a microcable 90 to a signal processor 92 located outside the patient. The catheter 78b ends in a three-part junction 94 of conventional construction that couples the catheter to an inflation source 96, a guide wire lumen and the signal processor 92. The inflation and guide wire ports 94a and 94b, respectively, are of conventional PTCA catheter construction. The third port 94c provides a path for the cable 90 to connect with the signal processor 92 and video display 88 via an electronic connector 98.

It should be noted that the present invention can be incorporated into a wide variety of ultrasound imaging catheter assemblies. For example, the present invention may be incorporated in a probe assembly mounted upon a diagnostic catheter that does not include a balloon. In addition, the probe assembly may also be mounted in the manner taught in Proudian et al. U.S. Pat. No. 4,917,097 and Eberle et al. U.S. Pat. No. 5,167,233, the teachings of which are explicitly incorporated, in all respects, herein by reference. These are only examples of various mounting configurations. Other configurations would be known to those skilled in the area of catheter design.

Furthermore, the preferred ultrasound transducer assembly embodying the present invention is on the order of a fraction of a millimeter to several millimeters in order to fit within the relatively small cross-section of blood vessels. However, the structure and method for manufacturing an ultrasound transducer assembly in accordance with present invention may be incorporated within larger ultrasound devices such as those used for lower gastrointestinal examinations.

Illustrative embodiments of the present invention have been provided. However, the scope of the present invention is intended to include, without limitation, any other modifications to the described ultrasound transducer device and methods of producing the device falling within the fullest legal scope of the present invention in view of the description of the invention and/or various preferred and alternative embodiments described herein. The intent is to cover all alternatives, modifications and equivalents included within the spirit and scope of the invention as defined by the appended claims.

What is claimed is:

1. An ultrasound transducer assembly comprising:

integrated circuitry;

an ultrasound transducer array including a set of ultrasound transducer elements, each transducer element comprising transducer material;

a flexible circuit to which the ultrasound transducer array and the integrated circuitry are attached during fabrication of the ultrasound transducer assembly, the flexible circuit comprising a flexible substrate that provides a re-shapeable platform to which the integrated circuitry and transducer elements are attached, wherein the flexible substrate comprises surface discontinuities, and ones of the surface discontinuities are disposed between adjacent pairs of transducer elements of the ultrasound transducer array.

2. The ultrasound transducer assembly of claim 1 wherein a first transducer element of the set of transducer elements has a first lengthwise axis and a second transducer element of the set of transducer elements has a second lengthwise axis, and wherein the first lengthwise axis and the second lengthwise axis are substantially parallel.

3. The ultrasound transducer assembly of claim 2 wherein ones of the surface discontinuities extend lengthwise substantially parallel to the first lengthwise axis.

4. The ultrasound transducer assembly of claim 3 wherein the first transducer element has a first transducer element length along the first lengthwise axis, and a one of the surface discontinuities has a discontinuity length, the first transducer element length being less than the discontinuity length.

5. The ultrasound transducer assembly of claim 1 wherein ones of the surface discontinuities are formed by cutting completely through the flexible substrate.

6. The ultrasound transducer assembly of claim 1 wherein the flexible substrate has a first thickness, wherein individual ones of the surface discontinuities are formed by a groove within the flexible substrate, and wherein the groove has a depth that is less than the first thickness.

7. A method for fabricating an intravascular ultrasound transducer assembly comprising a flexible circuit, integrated circuitry, and a set of transducer elements, the method comprising the steps:

fabricating the flexible circuit comprising a flexible substrate and a set of electrically conductive lines formed on the flexible substrate;

fabricating a transducer sheet comprising a transducer material;

attaching the transducer sheet to the flexible circuit while the flexible circuit is in a substantially flat shape;

dicing the transducer sheet into a set of discrete transducer elements, wherein the dicing step also includes the step of forming surface discontinuities having a depth of at least 3 $\mu$m from a surface of the flexible substrate, and wherein ones of the surface discontinuities are disposed between adjacent transducer elements of the set of discrete transducer elements.

8. The method of claim 7 wherein the forming surface discontinuities step comprises forming discontinuities that extend completely through the flexible substrate.

9. The method of claim 7 wherein the dicing step is performed using a saw.

10. The method of claim 7 wherein the dicing step is performed using a laser.

* * * * *